(12) United States Patent
Link et al.

(10) Patent No.: US 11,464,625 B2
(45) Date of Patent: Oct. 11, 2022

(54) TORIC SMALL APERTURE INTRAOCULAR LENS WITH EXTENDED DEPTH OF FOCUS

(71) Applicant: AcuFocus, Inc., Irvine, CA (US)

(72) Inventors: William J. Link, Steamboat Springs, CO (US); R. Kyle Webb, Carlsbad, CA (US)

(73) Assignee: AcuFocus, Inc., Irvine, CA (US)

( * ) Notice: Subject to any disclaimer, the term of this patent is extended or adjusted under 35 U.S.C. 154(b) by 409 days.

(21) Appl. No.: 15/775,158

(22) PCT Filed: Nov. 21, 2016

(86) PCT No.: PCT/US2016/063181
§ 371 (c)(1),
(2) Date: May 10, 2018

(87) PCT Pub. No.: WO2017/091520
PCT Pub. Date: Jun. 1, 2017

(65) Prior Publication Data
US 2018/0338826 A1    Nov. 29, 2018

Related U.S. Application Data

(60) Provisional application No. 62/259,524, filed on Nov. 24, 2015.

(51) Int. Cl.
*A61F 2/16* (2006.01)
(52) U.S. Cl.
CPC .......... *A61F 2/1645* (2015.04); *A61F 2/1624* (2013.01); *A61F 2002/1696* (2015.04);
(Continued)

(58) Field of Classification Search
CPC .................. A61F 2/1645; A61F 2/1624; A61F 2002/1696; A61F 2002/1699;
(Continued)

(56) References Cited

U.S. PATENT DOCUMENTS

| 2,350,421 A | 6/1944 | Schoder et al. |
| 2,470,927 A | 5/1949 | Hale, Jr. |

(Continued)

FOREIGN PATENT DOCUMENTS

| AU | 2004201751 | 5/2004 |
| CN | 1734305 A | 2/2006 |

(Continued)

OTHER PUBLICATIONS

"Extending Depth of Focus with Small Aperture Optics", AcuFocus, IC 8, Small Aperture IOL, Jul. 2019, in pp. 2.
(Continued)

*Primary Examiner* — Jennifer Dieterle
*Assistant Examiner* — Tiffany P Shipmon
(74) *Attorney, Agent, or Firm* — Knobbe, Martens, Olson & Bear, LLP

(57) ABSTRACT

An intraocular lens is provided that includes a refractive element and a mask. The refractive element has a first power in a first meridian and a second power greater than the first power in a second meridian. A magnitude of the first and second powers and a location of the first and second meridians are configured to correct astigmatism in a human eye. The mask is configured to block a substantial portion of light from passing through an annular region thereof and to permit a substantial portion of light to pass through a central aperture thereof to enhance an astigmatism correction rotational misplacement range and depth of focus.

16 Claims, 12 Drawing Sheets

(52) U.S. Cl.
CPC ............... *A61F 2002/1699* (2015.04); *A61F 2250/0071* (2013.01)

(58) Field of Classification Search
CPC .. B29D 11/00019; G02C 7/045; G02C 7/046; G02C 7/16
USPC .................................... 623/6.29; 351/159.14
See application file for complete search history.

(56) References Cited

U.S. PATENT DOCUMENTS

| | | |
|---|---|---|
| 3,034,403 A | 5/1962 | Neefe |
| 3,270,099 A | 8/1966 | Camp |
| 3,458,870 A | 8/1969 | Stone |
| 3,578,850 A | 5/1971 | Grant |
| 3,776,230 A | 12/1973 | Neefe |
| 3,794,414 A | 2/1974 | Wesley |
| 3,877,502 A | 4/1975 | Hunckler |
| 3,996,627 A | 12/1976 | Deeg et al. |
| 4,010,496 A | 3/1977 | Neefe |
| 4,104,338 A | 8/1978 | Guerrieri |
| 4,116,439 A | 9/1978 | Chavarrla et al. |
| 4,210,391 A | 7/1980 | Cohen |
| 4,298,996 A | 11/1981 | Barnet |
| 4,340,283 A | 7/1982 | Cohen |
| 4,402,396 A | 9/1983 | Graham |
| 4,402,579 A | 9/1983 | Poler |
| 4,423,728 A | 1/1984 | Lieberman |
| 4,435,050 A | 3/1984 | Poler |
| 4,450,593 A | 5/1984 | Poler |
| 4,470,159 A | 9/1984 | Peyman |
| 4,505,855 A | 3/1985 | Bruns et al. |
| 4,512,039 A | 4/1985 | Lieberman |
| 4,563,565 A | 1/1986 | Kampfer et al. |
| 4,575,373 A | 3/1986 | Johnson |
| 4,596,578 A | 6/1986 | Kelman |
| 4,607,617 A | 8/1986 | Choyce |
| 4,624,669 A | 11/1986 | Grendahl |
| 4,639,105 A | 1/1987 | Neefe |
| 4,646,720 A | 3/1987 | Peyman et al. |
| 4,655,774 A | 4/1987 | Choyce |
| 4,665,913 A | 5/1987 | Esperance, Jr. |
| 4,669,466 A | 6/1987 | L'Esperance |
| 4,669,834 A | 6/1987 | Richter |
| 4,676,790 A | 6/1987 | Kern |
| 4,676,791 A | 6/1987 | LeMaster et al. |
| 4,678,422 A | 7/1987 | York |
| 4,701,038 A | 10/1987 | Neefe |
| 4,715,858 A | 12/1987 | Lindstrom |
| 4,744,647 A | 5/1988 | Meshel et al. |
| 4,767,647 A | 8/1988 | Bree |
| 4,795,462 A * | 1/1989 | Grendahl ............... A61F 2/1618 351/159.14 |
| 4,798,608 A | 1/1989 | Grendahl |
| 4,799,784 A | 1/1989 | Safir |
| 4,799,931 A | 1/1989 | Lindstrom |
| 4,807,623 A | 2/1989 | Lieberman |
| 4,813,955 A | 3/1989 | Achatz et al. |
| 4,815,690 A | 3/1989 | Shepherd |
| 4,817,789 A | 4/1989 | Paul |
| 4,830,855 A | 5/1989 | Stewart |
| 4,842,599 A | 6/1989 | Bronstein |
| 4,842,782 A | 6/1989 | Portney |
| 4,851,003 A | 7/1989 | Lindstrom |
| 4,863,466 A | 9/1989 | Schlegel |
| 4,881,860 A | 11/1989 | Kanazawa |
| 4,903,695 A | 2/1990 | Warner et al. |
| 4,907,586 A | 3/1990 | Bille et al. |
| 4,928,815 A | 5/1990 | Paul |
| 4,955,904 A | 9/1990 | Atebara et al. |
| 4,976,732 A | 12/1990 | Vorosmarthy |
| 4,994,080 A | 2/1991 | Shepard |
| 5,013,319 A | 5/1991 | Davis |
| 5,030,230 A | 7/1991 | White |
| 5,034,166 A | 7/1991 | Rawlings et al. |
| 5,041,133 A | 8/1991 | Sayano et al. |
| 5,055,602 A | 10/1991 | Melpolder |
| 5,087,015 A | 2/1992 | Galley |
| 5,090,955 A | 2/1992 | Simon |
| 5,092,880 A | 3/1992 | Ohmi |
| 5,094,521 A | 3/1992 | Jolson et al. |
| 5,098,443 A | 3/1992 | Parel et al. |
| 5,108,427 A | 4/1992 | Majercik et al. |
| 5,112,328 A | 5/1992 | Taboada et al. |
| 5,120,120 A | 6/1992 | Cohen |
| 5,120,121 A | 6/1992 | Rawlings et al. |
| 5,137,441 A | 8/1992 | Fogarty |
| 5,147,395 A | 9/1992 | Willis |
| 5,171,318 A | 12/1992 | Gibson et al. |
| 5,185,107 A | 2/1993 | Blake |
| 5,188,494 A | 2/1993 | Hatin |
| 5,192,316 A | 3/1993 | Ting |
| 5,196,026 A | 3/1993 | Barrett et al. |
| 5,213,749 A | 5/1993 | Huss et al. |
| 5,260,727 A | 11/1993 | Oksman et al. |
| 5,266,241 A | 11/1993 | Parekh |
| 5,269,795 A | 12/1993 | Arnott |
| 5,269,812 A | 12/1993 | White |
| 5,274,404 A | 12/1993 | Michael |
| 5,288,436 A | 2/1994 | Liu et al. |
| 5,290,892 A | 3/1994 | Namdaran et al. |
| 5,292,514 A | 3/1994 | Capecchi et al. |
| 5,300,116 A | 4/1994 | Chirila et al. |
| 5,312,330 A | 5/1994 | Klopotek |
| 5,314,439 A | 5/1994 | Sugita |
| 5,314,961 A | 5/1994 | Anton et al. |
| 5,332,802 A | 7/1994 | Kelman et al. |
| 5,336,261 A | 8/1994 | Barrett et al. |
| 5,354,331 A | 10/1994 | Schachar et al. |
| 5,358,520 A | 10/1994 | Patel |
| 5,372,580 A | 12/1994 | Simon et al. |
| 5,391,201 A | 2/1995 | Barrett et al. |
| 5,441,511 A | 8/1995 | Hanna |
| 5,474,548 A | 12/1995 | Knopp et al. |
| 5,507,740 A | 4/1996 | O'Donnell, Jr. |
| 5,507,806 A | 4/1996 | Blake |
| 5,547,468 A | 4/1996 | Simon et al. |
| D375,245 S | 11/1996 | Irving |
| 5,578,080 A | 11/1996 | McDonald |
| 5,603,774 A | 2/1997 | LeBoeuf et al. |
| 5,607,437 A | 3/1997 | Simon et al. |
| 5,624,456 A | 4/1997 | Hellenkamp |
| 5,627,613 A | 5/1997 | Kaneko |
| 5,628,794 A | 5/1997 | Lindstrom |
| 5,628,795 A | 5/1997 | Langerman |
| 5,647,865 A | 7/1997 | Swinger |
| 5,652,638 A | 7/1997 | Roffman et al. |
| 5,653,752 A | 8/1997 | Silvestrini et al. |
| 5,662,706 A | 9/1997 | Legerton et al. |
| 5,674,284 A | 10/1997 | Chang et al. |
| 5,693,268 A | 12/1997 | Widman et al. |
| 5,697,923 A | 12/1997 | Poler |
| 5,702,440 A | 12/1997 | Portney |
| 5,708,049 A | 1/1998 | Katagiri et al. |
| 5,713,957 A | 2/1998 | Steele et al. |
| 5,722,971 A | 3/1998 | Peyman |
| 5,725,575 A | 3/1998 | O'Donnell, Jr. |
| 5,728,156 A | 3/1998 | Gupta et al. |
| 5,746,558 A | 5/1998 | Nygren et al. |
| 5,752,967 A | 5/1998 | Kritzinger et al. |
| 5,757,458 A | 5/1998 | Miller et al. |
| 5,769,889 A | 6/1998 | Kelman |
| 5,774,202 A | 6/1998 | Abraham et al. |
| 5,786,883 A | 7/1998 | Miller et al. |
| 5,824,086 A | 10/1998 | Silvestrini |
| 5,837,156 A | 11/1998 | Cumming |
| 5,843,105 A | 12/1998 | Mathis et al. |
| 5,864,128 A | 1/1999 | Plesko |
| 5,870,167 A | 2/1999 | Knopp et al. |
| 5,876,442 A | 3/1999 | Lipshitz et al. |
| 5,895,610 A | 4/1999 | Chang et al. |
| 5,905,561 A * | 5/1999 | Lee ..................... G02C 7/16 351/159.02 |
| 5,910,537 A | 6/1999 | Feingold et al. |

(56) References Cited

U.S. PATENT DOCUMENTS

| | | |
|---|---|---|
| 5,913,898 A | 6/1999 | Feingold et al. |
| 5,919,185 A | 7/1999 | Peyman |
| 5,925,294 A | 7/1999 | Shibuya |
| 5,964,748 A | 10/1999 | Peyman |
| 5,964,776 A | 10/1999 | Peyman |
| 5,965,330 A | 10/1999 | Evans et al. |
| 5,980,040 A | 11/1999 | Xu et al. |
| 6,007,579 A | 12/1999 | Lipshitz et al. |
| 6,017,121 A | 1/2000 | Chateau et al. |
| 6,063,073 A | 5/2000 | Peyman |
| 6,090,141 A | 7/2000 | Lindstrom |
| 6,102,946 A | 8/2000 | Nigam |
| 6,106,553 A | 8/2000 | Feingold et al. |
| 6,110,166 A | 8/2000 | Juhasz et al. |
| 6,138,307 A | 10/2000 | McDonald |
| 6,152,959 A | 11/2000 | Portney |
| 6,164,777 A | 12/2000 | Li et al. |
| 6,171,336 B1 | 1/2001 | Sawusch |
| 6,178,593 B1 | 1/2001 | Carlson |
| 6,197,019 B1 | 3/2001 | Peyman |
| 6,201,036 B1 | 3/2001 | Fedorov et al. |
| 6,203,538 B1 | 3/2001 | Peyman |
| 6,210,401 B1 | 4/2001 | Lai |
| 6,217,571 B1 | 4/2001 | Peyman |
| 6,217,596 B1 | 4/2001 | Farah |
| 6,221,067 B1 | 4/2001 | Peyman |
| 6,228,113 B1 | 5/2001 | Kaufman |
| 6,228,114 B1 | 5/2001 | Lee |
| 6,228,115 B1 | 5/2001 | Hoffmann et al. |
| 6,264,648 B1 | 7/2001 | Peyman |
| 6,277,146 B1 | 8/2001 | Peyman et al. |
| 6,280,470 B1 | 8/2001 | Peyman |
| 6,280,471 B1 | 8/2001 | Peyman et al. |
| 6,302,877 B1 | 10/2001 | Ruiz |
| 6,304,390 B1 | 10/2001 | Takanashi |
| 6,308,590 B1 | 10/2001 | Berto |
| 6,335,190 B1 | 1/2002 | Zhou et al. |
| 6,361,560 B1 | 3/2002 | Nigam |
| 6,376,153 B2 | 4/2002 | Uchikawa et al. |
| 6,387,379 B1 | 5/2002 | Goldberg et al. |
| 6,391,230 B1 | 5/2002 | Sarbadhikari |
| 6,416,179 B1 | 7/2002 | Lieberman et al. |
| 6,423,093 B1 | 7/2002 | Hicks et al. |
| 6,432,246 B1 | 8/2002 | Blake |
| 6,436,092 B1 | 8/2002 | Peyman |
| 6,458,141 B1 | 10/2002 | Peyman |
| 6,461,384 B1 | 10/2002 | Hoffmann et al. |
| 6,469,844 B1 | 10/2002 | Iwase et al. |
| 6,480,346 B2 | 11/2002 | Funakoshi |
| 6,491,637 B2 | 12/2002 | Foster et al. |
| 6,497,700 B1 | 12/2002 | LaHaye |
| 6,515,006 B2 | 2/2003 | Horn |
| 6,533,416 B1 | 3/2003 | Fermigier et al. |
| 6,551,307 B2 | 4/2003 | Peyman |
| 6,554,424 B1 | 4/2003 | Miller et al. |
| 6,554,860 B2 | 4/2003 | Hoffmann et al. |
| 6,555,103 B2 | 4/2003 | Leukel et al. |
| 6,575,573 B2 | 6/2003 | Lai et al. |
| 6,581,993 B2 | 6/2003 | Nigam |
| 6,588,902 B2 | 7/2003 | Isogai |
| 6,589,280 B1 | 7/2003 | Koziol |
| 6,607,527 B1 | 8/2003 | Ruiz et al. |
| 6,613,088 B1 | 9/2003 | Babizhayev |
| 6,638,304 B2 | 10/2003 | Azar |
| 6,649,722 B2 | 11/2003 | Rosenzweig et al. |
| 6,655,804 B2 | 12/2003 | Streibig |
| 6,692,126 B1 | 2/2004 | Xie et al. |
| 6,702,807 B2 | 3/2004 | Peyman |
| 6,726,322 B2 | 4/2004 | Andino et al. |
| 6,740,116 B2 | 5/2004 | Morcher |
| 6,755,858 B1 | 6/2004 | White |
| 6,786,926 B2 | 9/2004 | Peyman |
| 6,811,256 B1 | 11/2004 | Becherer et al. |
| 6,855,163 B2 | 2/2005 | Peyman |
| 6,874,886 B2 | 4/2005 | Miller et al. |
| 6,899,424 B2 | 5/2005 | Miller et al. |
| 6,949,093 B1 | 9/2005 | Peyman |
| 6,951,556 B2 | 10/2005 | Epstein |
| 6,966,648 B2 | 11/2005 | Miller et al. |
| 6,989,008 B2 | 1/2006 | Peyman |
| 6,997,428 B1 | 2/2006 | Andino et al. |
| 7,001,374 B2 | 2/2006 | Peyman |
| 7,008,447 B2 | 3/2006 | Koziol |
| 7,025,455 B2 | 4/2006 | Roffman |
| 7,061,693 B2 | 6/2006 | Zalevsky |
| 7,099,057 B2 | 8/2006 | Parker et al. |
| 7,276,080 B2 | 10/2007 | Murakami et al. |
| 7,287,852 B2 | 10/2007 | Fiala |
| 7,364,674 B1 | 4/2008 | Hoover |
| 7,399,811 B2 | 7/2008 | Mentak et al. |
| 7,404,637 B2 | 7/2008 | Miller et al. |
| 7,404,638 B2 | 7/2008 | Miller et al. |
| 7,446,157 B2 | 11/2008 | Mentak et al. |
| 7,455,404 B2 | 11/2008 | Bandhauer et al. |
| 7,455,691 B2 | 11/2008 | Feingold et al. |
| 7,462,193 B2 | 12/2008 | Nagamoto |
| 7,477,452 B2 | 1/2009 | Tsuruma |
| 7,491,350 B2 | 1/2009 | Silvestrini |
| 7,497,866 B2 | 3/2009 | Perez |
| 7,628,810 B2 | 12/2009 | Christie et al. |
| 7,632,431 B2 | 12/2009 | Ghazizadeh et al. |
| 7,641,337 B2 | 1/2010 | Altmann |
| 7,645,299 B2 | 1/2010 | Koziol |
| 7,745,555 B2 | 6/2010 | Mentak et al. |
| 7,780,290 B2 | 8/2010 | Zhao |
| 7,842,367 B2 | 11/2010 | Mentak |
| 7,976,577 B2 | 7/2011 | Silvestrini |
| D645,337 S | 9/2011 | Hsu et al. |
| 8,043,371 B2 | 10/2011 | Paul et al. |
| 8,048,972 B2 | 11/2011 | Mentak et al. |
| 8,079,706 B2 | 12/2011 | Silvestrini et al. |
| D656,526 S | 3/2012 | Christie et al. |
| 8,157,374 B2 | 4/2012 | Bandhauer et al. |
| 8,241,354 B2 | 8/2012 | Hong et al. |
| 8,287,592 B2 | 10/2012 | Silvestrini |
| 8,343,215 B2 | 1/2013 | Miller et al. |
| D681,086 S | 4/2013 | Christie et al. |
| 8,420,753 B2 | 4/2013 | Mentak et al. |
| 8,439,498 B2 | 5/2013 | Zhao et al. |
| 8,460,374 B2 | 6/2013 | Christie et al. |
| 8,562,131 B2 | 10/2013 | Zhao |
| 8,604,098 B2 | 12/2013 | Boydston et al. |
| 8,740,978 B2 | 6/2014 | Weeber et al. |
| 8,747,466 B2 | 6/2014 | Weeber et al. |
| 8,752,958 B2 | 6/2014 | Miller et al. |
| 8,633,292 B2 | 7/2014 | Hu et al. |
| 8,814,934 B2 | 8/2014 | Geraghty et al. |
| 8,858,624 B2 | 10/2014 | Christie et al. |
| 8,864,824 B2 | 10/2014 | Silvestrini et al. |
| 8,955,968 B2 | 2/2015 | Zalevsky et al. |
| 9,005,281 B2 | 4/2015 | Christie et al. |
| 9,138,142 B2 | 9/2015 | Christie et al. |
| 9,204,962 B2 | 12/2015 | Silvestrini |
| 9,358,103 B1 * | 6/2016 | Wortz .................. A61F 2/14 |
| 9,427,311 B2 | 8/2016 | Christie et al. |
| 9,427,922 B2 | 8/2016 | Reboul et al. |
| 9,492,272 B2 | 11/2016 | Christie et al. |
| 9,545,303 B2 | 1/2017 | Vilupuru et al. |
| 9,573,328 B2 | 2/2017 | Reboul et al. |
| 9,603,704 B2 | 3/2017 | Silvestrini |
| 9,744,077 B2 | 8/2017 | Zicker et al. |
| 9,757,227 B2 | 9/2017 | Kushlin et al. |
| 9,844,919 B2 | 12/2017 | Reboul et al. |
| 9,848,979 B2 | 12/2017 | Vilupuru et al. |
| 9,943,403 B2 | 4/2018 | Webb et al. |
| 9,987,127 B2 | 6/2018 | Bogaert et al. |
| 10,004,593 B2 | 6/2018 | Webb et al. |
| 10,183,453 B2 | 1/2019 | Reboul et al. |
| 10,342,656 B2 | 7/2019 | Vilupuru et al. |
| 10,350,058 B2 | 7/2019 | Silvestrini |
| 10,426,600 B2 | 10/2019 | Coleman et al. |
| 10,449,036 B2 | 10/2019 | Christie et al. |
| 10,548,717 B2 | 2/2020 | Webb et al. |
| 10,583,619 B2 | 3/2020 | Reboul et al. |

(56) References Cited

U.S. PATENT DOCUMENTS

| | | |
|---|---|---|
| 10,687,935 B2 | 6/2020 | Webb et al. |
| 10,765,508 B2 | 9/2020 | Vilupuru et al. |
| 10,869,752 B2 | 12/2020 | Christie et al. |
| 10,932,902 B2 | 3/2021 | Reedy et al. |
| 10,939,995 B2 | 3/2021 | Silvestrini |
| 11,311,371 B2 | 4/2022 | Webb et al. |
| 11,357,617 B2 | 6/2022 | Christie et al. |
| 11,364,110 B2 | 6/2022 | Webb |
| 2001/0027314 A1 | 10/2001 | Peyman |
| 2001/0034516 A1 | 10/2001 | Peyman |
| 2001/0040740 A1 | 11/2001 | Funakoshi |
| 2001/0050750 A1 | 12/2001 | Breger |
| 2002/0010510 A1 | 1/2002 | Silvestrini |
| 2002/0082288 A1 | 6/2002 | Horn |
| 2002/0120329 A1 | 8/2002 | Lang et al. |
| 2002/0128710 A1 | 9/2002 | Eggleston |
| 2002/0167640 A1 | 11/2002 | Francis et al. |
| 2002/0196409 A1 | 12/2002 | Jani |
| 2003/0014042 A1 | 1/2003 | Juhasz et al. |
| 2003/0060880 A1 | 3/2003 | Feingold |
| 2003/0105521 A1 | 6/2003 | Perez |
| 2003/0135272 A1 | 7/2003 | Brady et al. |
| 2003/0149480 A1 | 8/2003 | Shadduck |
| 2003/0204258 A1 | 10/2003 | Graham et al. |
| 2003/0216763 A1 | 11/2003 | Patel |
| 2004/0019379 A1 | 1/2004 | Glick et al. |
| 2004/0056371 A1 | 3/2004 | Liao et al. |
| 2004/0068317 A1 | 4/2004 | Knight |
| 2004/0106929 A1 | 6/2004 | Masket |
| 2004/0140578 A1 | 7/2004 | Kelly et al. |
| 2005/0027355 A1 | 2/2005 | Murakami et al. |
| 2005/0046794 A1 | 3/2005 | Silvestrini et al. |
| 2005/0056954 A1 | 3/2005 | Devlin |
| 2005/0090895 A1 | 4/2005 | Peyman |
| 2005/0124983 A1 | 6/2005 | Frey et al. |
| 2005/0134793 A1 | 6/2005 | Roffman |
| 2005/0137703 A1 | 6/2005 | Chen |
| 2005/0143751 A1 | 6/2005 | Makker et al. |
| 2005/0143813 A1 | 6/2005 | Hovey et al. |
| 2005/0182488 A1 | 8/2005 | Peyman |
| 2005/0182489 A1 | 8/2005 | Peyman |
| 2005/0187621 A1 | 8/2005 | Brady |
| 2005/0288784 A1 | 12/2005 | Peyman |
| 2006/0064077 A1 | 3/2006 | Peyman |
| 2006/0079959 A1 | 4/2006 | Christie et al. |
| 2006/0113054 A1 | 6/2006 | Silvestrini |
| 2006/0135477 A1 | 6/2006 | Haitjema et al. |
| 2006/0184243 A1 | 8/2006 | Yilmaz |
| 2006/0232665 A1 | 10/2006 | Schowengerdt et al. |
| 2006/0235428 A1 | 10/2006 | Silvestrini |
| 2006/0235514 A1 | 10/2006 | Silvestrini |
| 2006/0241751 A1 | 10/2006 | Marmo et al. |
| 2006/0247659 A1 | 11/2006 | Moeller et al. |
| 2006/0265058 A1 | 11/2006 | Silvestrini |
| 2006/0268226 A1 | 11/2006 | Christie et al. |
| 2006/0268227 A1 | 11/2006 | Christie et al. |
| 2006/0268228 A1 | 11/2006 | Christie et al. |
| 2006/0268229 A1 | 11/2006 | Silvestrini et al. |
| 2006/0270946 A1 | 11/2006 | Silvestrini et al. |
| 2006/0271026 A1 | 11/2006 | Silvestrini et al. |
| 2006/0271178 A1 | 11/2006 | Christie et al. |
| 2006/0271179 A1 | 11/2006 | Christie et al. |
| 2006/0271180 A1 | 11/2006 | Christie et al. |
| 2006/0271181 A1 | 11/2006 | Christie et al. |
| 2006/0271182 A1 | 11/2006 | Christie et al. |
| 2006/0271183 A1 | 11/2006 | Christie et al. |
| 2006/0271184 A1 | 11/2006 | Silvestrini |
| 2006/0271185 A1 | 11/2006 | Silvestrini |
| 2006/0274264 A1 | 12/2006 | Christie et al. |
| 2006/0274265 A1 | 12/2006 | Christie et al. |
| 2007/0021832 A1 | 1/2007 | Nordan |
| 2007/0032866 A1 | 2/2007 | Portney |
| 2007/0091472 A1 | 4/2007 | Alkemper et al. |
| 2007/0092592 A1 | 4/2007 | Chiang |
| 2007/0129797 A1 | 6/2007 | Lang et al. |
| 2007/0225691 A1 | 9/2007 | Silvestrini et al. |
| 2008/0033546 A1 | 2/2008 | Liang |
| 2008/0077238 A1 | 3/2008 | Deacon et al. |
| 2008/0100921 A1 | 5/2008 | Nishikawa |
| 2008/0151183 A1 | 6/2008 | Altmann |
| 2008/0208335 A1 | 8/2008 | Blum et al. |
| 2008/0212030 A1 | 9/2008 | Bentley et al. |
| 2008/0220214 A1 | 9/2008 | Uozu et al. |
| 2008/0221674 A1 | 9/2008 | Blum et al. |
| 2008/0221676 A1 | 9/2008 | Coleman et al. |
| 2008/0255663 A1 | 10/2008 | Akpek et al. |
| 2008/0269884 A1 | 10/2008 | Vannoy |
| 2008/0306587 A1 | 12/2008 | Your |
| 2009/0012505 A1 | 1/2009 | Chernyak |
| 2009/0021692 A1 | 1/2009 | Miller et al. |
| 2009/0287306 A1 | 1/2009 | Smith et al. |
| 2009/0036880 A1 | 2/2009 | Bischoff et al. |
| 2009/0048608 A1 | 2/2009 | Boukhny et al. |
| 2009/0059168 A1 | 3/2009 | Miller et al. |
| 2009/0069817 A1 | 3/2009 | Peyman |
| 2009/0164008 A1 | 6/2009 | Hong et al. |
| 2009/0171458 A1 | 7/2009 | Kellan et al. |
| 2009/0187242 A1 | 7/2009 | Weeber et al. |
| 2009/0204207 A1 | 8/2009 | Blum et al. |
| 2009/0213326 A1 | 8/2009 | Zhao |
| 2009/0222086 A1 | 9/2009 | Lui et al. |
| 2009/0234448 A1 | 9/2009 | Weeber et al. |
| 2009/0279048 A1 | 11/2009 | Hong et al. |
| 2009/0306773 A1 | 12/2009 | Silvestrini et al. |
| 2009/0323020 A1* | 12/2009 | Zhao .................... G02C 7/044 351/159.44 |
| 2010/0016961 A1 | 1/2010 | Hong et al. |
| 2010/0016965 A1 | 1/2010 | Hong et al. |
| 2010/0082017 A1 | 4/2010 | Zickler et al. |
| 2010/0082100 A1 | 4/2010 | Mikawa |
| 2010/0127412 A1 | 5/2010 | Lake |
| 2010/0149618 A1 | 6/2010 | Sprague |
| 2010/0208199 A1 | 8/2010 | Levis et al. |
| 2010/0225014 A1 | 9/2010 | Bille |
| 2010/0312336 A1 | 12/2010 | Hong et al. |
| 2011/0029074 A1 | 2/2011 | Reisin et al. |
| 2011/0037184 A1 | 2/2011 | Shoji et al. |
| 2011/0040376 A1* | 2/2011 | Christie ................... A61F 2/15 623/6.17 |
| 2011/0051080 A1 | 3/2011 | Bandhauer et al. |
| 2011/0125261 A1 | 5/2011 | Portney |
| 2011/0140333 A1 | 6/2011 | Schaper et al. |
| 2011/0166652 A1* | 7/2011 | Bogaert ................ A61F 2/1654 623/6.27 |
| 2011/0172675 A1 | 7/2011 | Danta et al. |
| 2011/0245919 A1 | 10/2011 | Pettit |
| 2011/0251685 A1 | 10/2011 | Chu |
| 2011/0292340 A1 | 12/2011 | Shimizu et al. |
| 2012/0143325 A1* | 6/2012 | Christie ................ G02C 7/046 623/5.13 |
| 2012/0203239 A1 | 8/2012 | Vukich et al. |
| 2012/0245683 A1 | 9/2012 | Christie et al. |
| 2012/0309761 A1 | 12/2012 | Chow et al. |
| 2012/0310338 A1 | 12/2012 | Christie et al. |
| 2013/0053953 A1 | 2/2013 | Silvestrini |
| 2013/0131795 A1 | 5/2013 | Miller et al. |
| 2013/0147072 A1 | 6/2013 | Bothe et al. |
| 2013/0190868 A1 | 7/2013 | Kahook et al. |
| 2013/0238091 A1 | 9/2013 | Danta et al. |
| 2013/0289543 A1 | 10/2013 | Mordaunt |
| 2013/0324983 A1 | 12/2013 | Liang |
| 2014/0121767 A1 | 5/2014 | Simpson |
| 2014/0131905 A1 | 5/2014 | Webb |
| 2014/0200666 A1 | 7/2014 | Phillips |
| 2014/0277437 A1* | 9/2014 | Currie ................... A61F 2/1624 623/6.37 |
| 2014/0336625 A1 | 11/2014 | Fernandez |
| 2014/0343541 A1 | 11/2014 | Scott et al. |
| 2014/0379078 A1 | 12/2014 | Trindade |
| 2015/0025627 A1 | 1/2015 | Christie et al. |
| 2015/0046094 A1 | 2/2015 | Chaudhary et al. |
| 2015/0073549 A1 | 3/2015 | Webb et al. |
| 2015/0177422 A1 | 6/2015 | Liu et al. |
| 2015/0183173 A1 | 7/2015 | Linhardt et al. |

(56) References Cited

U.S. PATENT DOCUMENTS

| | | |
|---|---|---|
| 2015/0250583 A1 | 9/2015 | Rosen et al. |
| 2015/0366658 A1 | 12/2015 | Christie et al. |
| 2016/0100938 A1 | 4/2016 | Bogaert et al. |
| 2016/0297107 A1 | 10/2016 | Shim et al. |
| 2017/0049560 A1 | 2/2017 | Cherne |
| 2017/0143477 A1 | 5/2017 | Christie et al. |
| 2017/0156850 A1 | 6/2017 | Silvestrini et al. |
| 2018/0125639 A1 | 5/2018 | Vilupuru et al. |
| 2018/0133990 A1 | 5/2018 | Reboul et al. |
| 2018/0296322 A1 | 10/2018 | Webb et al. |
| 2019/0076235 A1 | 3/2019 | Webb et al. |
| 2019/0076241 A1 | 3/2019 | Alarcon Heredia et al. |
| 2019/0193350 A1 | 6/2019 | Gu et al. |
| 2019/0269499 A1 | 9/2019 | Ellis |
| 2020/0000576 A1 | 1/2020 | Christie et al. |
| 2020/0008932 A1 | 1/2020 | Silvestrini |
| 2020/0179105 A1 | 6/2020 | Waterhouse et al. |
| 2020/0253721 A1 | 8/2020 | Cuevas et al. |
| 2020/0337831 A1 | 10/2020 | Webb et al. |
| 2020/0337834 A1 | 10/2020 | Webb et al. |
| 2021/0015604 A1 | 1/2021 | Ma |
| 2021/0137674 A1 | 5/2021 | Webb |
| 2021/0154002 A1 | 5/2021 | Christie et al. |
| 2021/0244532 A1 | 8/2021 | Silvestrini |
| 2021/0290373 A1 | 9/2021 | Peyman et al. |

FOREIGN PATENT DOCUMENTS

| | | |
|---|---|---|
| CN | 1875895 | 12/2006 |
| CN | 100368846 | 2/2008 |
| CN | 101322663 | 12/2008 |
| CN | 102448404 | 5/2012 |
| CN | 101341426 B | 7/2012 |
| CN | 203647535 U | 6/2014 |
| DE | 2727410 A1 | 12/1978 |
| DE | 4134320 | 4/1992 |
| EP | 0165652 | 12/1985 |
| EP | 0443094 | 8/1991 |
| EP | 1173790 | 1/2002 |
| EP | 1674049 | 6/2006 |
| EP | 1548489 B1 | 8/2006 |
| EP | 2111822 | 10/2009 |
| EP | 2319457 | 5/2011 |
| EP | 2243052 B1 | 9/2011 |
| EP | 2365379 | 9/2011 |
| EP | 2455799 | 5/2012 |
| EP | 2823789 | 1/2015 |
| EP | 2364457 B1 | 8/2015 |
| EP | 2993514 A1 | 3/2016 |
| EP | 2349150 B1 | 7/2016 |
| FR | 2620687 | 3/1989 |
| FR | 2649605 | 1/1991 |
| GB | 1276003 | 6/1972 |
| GB | 2507465 | 5/2014 |
| JP | 62-167343 | 7/1987 |
| JP | 64-002644 | 1/1989 |
| JP | H01-195852 | 8/1989 |
| JP | H02-7954 | 1/1990 |
| JP | 04-158859 | 6/1992 |
| JP | 06-509731 | 3/1993 |
| JP | H05-65340 | 9/1993 |
| JP | 06-502782 | 3/1994 |
| JP | H07-067896 | 3/1995 |
| JP | 07-265340 | 10/1995 |
| JP | 08-103457 A | 4/1996 |
| JP | H09-502542 | 3/1997 |
| JP | 11-503657 | 8/1997 |
| JP | 07-178125 | 7/1998 |
| JP | 2000-047145 | 2/2000 |
| JP | 2002-537895 | 11/2002 |
| JP | 2003-502109 | 1/2003 |
| JP | 2004-510199 | 4/2004 |
| JP | 2004-538034 | 12/2004 |
| JP | 2005-533576 | 11/2005 |
| JP | 2007-516794 | 6/2007 |
| JP | 2007-523720 | 8/2007 |
| JP | 2008-506710 | 3/2008 |
| JP | S59-54527 | 5/2008 |
| JP | 2013-501598 | 1/2013 |
| JP | 2015-077412 | 4/2015 |
| KR | 10-0335722 | 5/2002 |
| KR | 10-2012-0093837 | 8/2012 |
| RU | 2138837 | 9/1999 |
| RU | 110978 U | 3/2011 |
| RU | 2456968 | 7/2012 |
| RU | 2457812 | 8/2012 |
| RU | 2459598 | 8/2012 |
| RU | 2493801 | 9/2013 |
| RU | 134049 | 11/2013 |
| RU | 134784 | 11/2013 |
| RU | 2500368 | 12/2013 |
| RU | 2511081 | 4/2014 |
| RU | 2517488 | 5/2014 |
| SU | 1380743 A1 | 3/1988 |
| TW | 201103518 | 2/2011 |
| WO | WO 87/05797 | 10/1987 |
| WO | WO 95/03747 | 2/1995 |
| WO | WO 95/08135 | 3/1995 |
| WO | WO 96/35397 | 11/1996 |
| WO | WO 98/48715 | 11/1998 |
| WO | WO 00/025704 | 5/2000 |
| WO | WO 00/038594 | 7/2000 |
| WO | WO 00/51682 | 9/2000 |
| WO | WO 00/52516 | 9/2000 |
| WO | WO 00/70388 | 11/2000 |
| WO | WO 2001/010641 | 2/2001 |
| WO | WO 01/15779 | 3/2001 |
| WO | WO 01/17460 | 3/2001 |
| WO | WO 01/19364 | 3/2001 |
| WO | WO 01/082815 | 11/2001 |
| WO | WO 02/076320 | 10/2002 |
| WO | WO 02/102241 | 12/2002 |
| WO | WO 03/020177 | 3/2003 |
| WO | WO 03/022168 | 3/2003 |
| WO | WO 03/061518 | 7/2003 |
| WO | WO 2004/014969 | 2/2004 |
| WO | WO 2004/034917 | 4/2004 |
| WO | WO 2004/105588 | 12/2004 |
| WO | WO 2004/113959 | 12/2004 |
| WO | WO 2005/023154 | 3/2005 |
| WO | WO 2005/082265 | 9/2005 |
| WO | WO 2006/014738 | 2/2006 |
| WO | WO 2006/020638 | 2/2006 |
| WO | WO 2006/047534 | 5/2006 |
| WO | WO 2006/060380 | 6/2006 |
| WO | WO 2006/069012 | 6/2006 |
| WO | WO 2006/113377 | 10/2006 |
| WO | WO 2006/113411 | 10/2006 |
| WO | WO 2006/113563 | 10/2006 |
| WO | WO 2006/113564 | 10/2006 |
| WO | WO 2007/057734 | 10/2007 |
| WO | WO 2007/133384 | 11/2007 |
| WO | WO 2007/142981 | 12/2007 |
| WO | WO 2008/036671 | 3/2008 |
| WO | WO 2008/102096 | 8/2008 |
| WO | WO 2009/050511 | 4/2009 |
| WO | WO 2009/122409 | 10/2009 |
| WO | WO 2009/140080 | 11/2009 |
| WO | WO 2009/149060 | 12/2009 |
| WO | WO 2010/002215 | 1/2010 |
| WO | WO 2010/059214 | 5/2010 |
| WO | WO 2010/118469 | 10/2010 |
| WO | WO 2011/020074 | 2/2011 |
| WO | WO 2011/020078 | 2/2011 |
| WO | WO 2011/047076 | 4/2011 |
| WO | WO 2011/069059 | 6/2011 |
| WO | WO 2011/088107 | 7/2011 |
| WO | WO 2012/170066 | 12/2012 |
| WO | WO 2011/030509 | 2/2013 |
| WO | WO 2013/019871 | 2/2013 |
| WO | WO 2013/082545 | 6/2013 |
| WO | WO 2013/101793 | 7/2013 |
| WO | WO 2013/112589 | 8/2013 |
| WO | WO 2013/123265 | 8/2013 |

(56) References Cited

FOREIGN PATENT DOCUMENTS

| WO | WO 2014/054946 | 4/2014 |
|---|---|---|
| WO | WO 2014/074610 | 5/2014 |
| WO | WO 2014/158653 | 10/2014 |
| WO | WO 2014/164056 | 10/2014 |
| WO | WO 2014/195059 | 12/2014 |
| WO | WO 2015/021323 | 2/2015 |
| WO | WO 2015/069927 | 5/2015 |
| WO | WO 2015/073718 | 5/2015 |
| WO | WO 2015/078271 | 6/2015 |
| WO | WO 2015/086611 | 6/2015 |
| WO | WO 2016/081493 | 5/2016 |
| WO | WO 2015/108156 | 3/2017 |
| WO | WO 2017/062316 | 4/2017 |
| WO | WO 2017/091520 | 6/2017 |
| WO | WO 2019/010178 | 1/2019 |

OTHER PUBLICATIONS

Internet Archive Wayback Machine; Aniridia Implants; downloaded from https://web.archive.org/web/20110824062840/http://www.morcher.com/nc/produkte/aniridiaimplants.html (Archived Aug. 24, 2011; printed on Feb. 5, 2015).

Guyton A.C., Textbook of Medical Physiology, 7th Edition, W.B. Saunders Company, Jan. 1986: Chapter 58, in 13 pages.

International Search Report and Written Opinion for PCT/US2016/63181 dated Mar. 31, 2017 in 9 pages.

Lu Xuequan, et al. "Radiation preparation and thermo-response swelling of interpenetrating polymer network hydrogel composed of PNIPAAm and PMMA", Radiation Physics and Chemistry, vol. 57, Mar. 2000, pp. 477-480, XP002473596.

Patel, C.K., et al. "Imaging the macula through a black occlusive intraocular lens". Arch. Ophthalmol. Oct. 2010; 128(10):1374-1376.

Yusuf, et al., "Inability to perform posterior segment monitoring by scanning laser ophthalmoscopy or optical coherence tomography with some occlusive intraocular lenses in clinical use", J. Cataract Refract. Surg., Mar. 2012, 38: 513-518.

Yusuf, et al., "Occlusive IOLs for Intractable Diplopia Demonstrate a Novel Near-Infrared Window of Transmission for SLO/OCT Imaging and Clinical Assessment". Investigative Ophthalmology & Visual Science, May 2011, 52(6): 3737-3743.

Reper-NN LTD, Instruction for Use. MOIL-Iris Iris-intaocular polymer elastic lenses, dated Aug. 2017, in 8 pages.

Ferrari et al. "La keratopigmentation annnulaire (ou PresbyRing) dans la prise en charge de la presbytie: etude experimentale de faisabilite post-mortem chez l'animal", Journal Francais d'Ophtalmologie, vol. 36, Issue 6, Jun. 2013, pp. 481-487.

\* cited by examiner

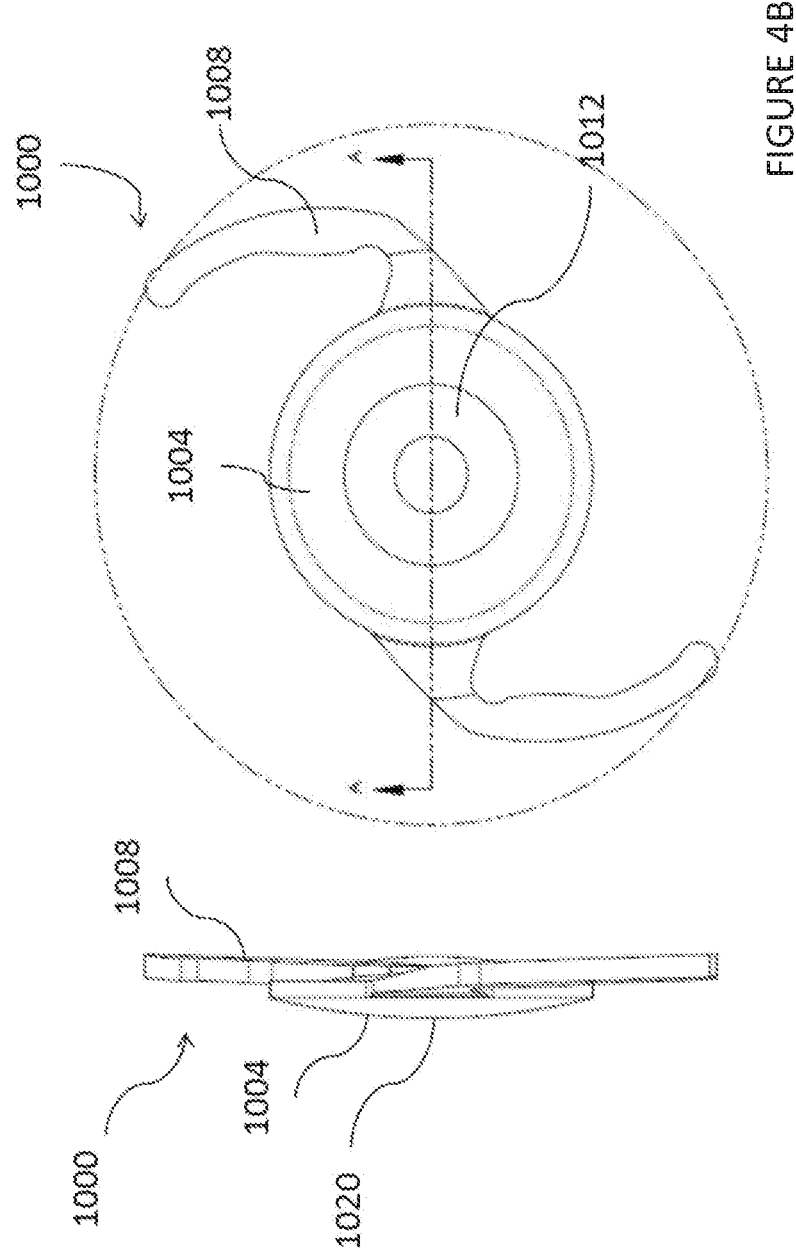

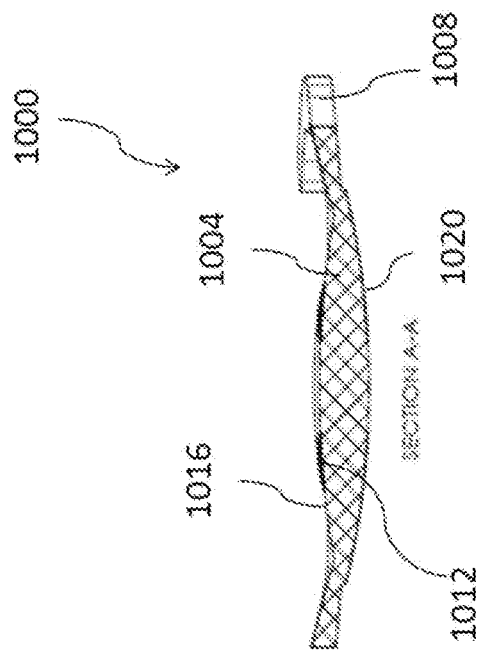
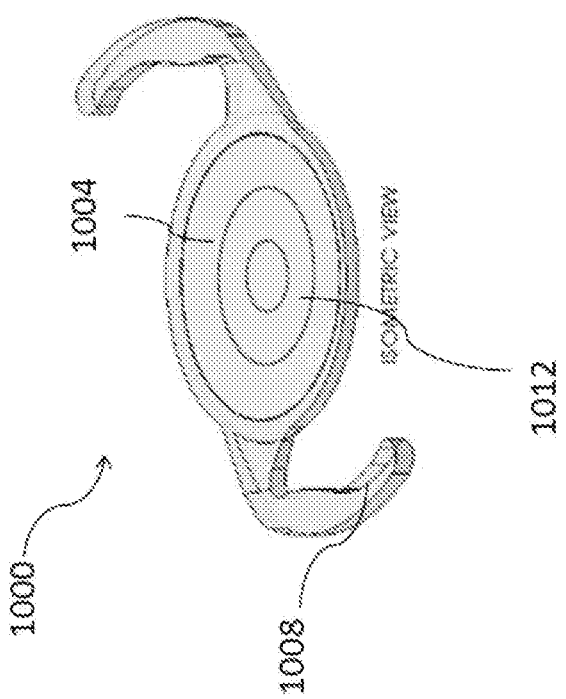

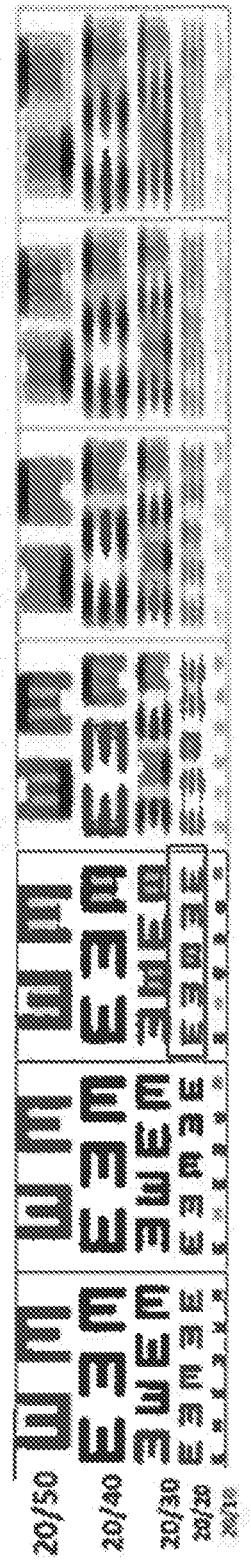
FIGURE 8

TORIC SMALL APERTURE INTRAOCULAR LENS WITH EXTENDED DEPTH OF FOCUS

RELATED APPLICATIONS

This application claims the benefit of U.S. Provisional Application No. 62/259,524, filed Nov. 24, 2015, which is hereby incorporated by reference in its entirety herein.

BACKGROUND

Field

This application is directed to ophthalmic devices that can be used to improve vision in patients suffering from astigmatism.

DESCRIPTION OF THE RELATED ART

The human eye functions to provide vision by transmitting and focusing light through the cornea and through the crystalline lens in the eye to form a focused image on a retina. The quality of the focused image depends on many factors including the size and shape of the eye, the transparency of the cornea and the lens, as well as the capability of the lens to accommodate.

The optical power of the eye is a function of the optical power of the cornea and the crystalline lens. In a normal, healthy eye, sharp images of distant objects are formed on the retina. This vision state is called emmetropia. In myopic eyes, images of distant objects are formed at a location in front of the retina. This may be because the eye is abnormally long or the cornea is abnormally steep. In hyperopic eyes, images are formed at a location behind the retina. This may be because the eye is abnormally short or the cornea is abnormally flat. The focusing effect of the eye may be rotationally asymmetric, resulting in an uncompensated cylindrical refractive error referred to as astigmatism.

Some people suffer from cataracts in which the crystalline lens undergoes a loss of transparency. In such cases, the crystalline lens can be removed and replaced with an intraocular lens (IOL). However, commercially approved intraocular lenses do not restore full vision function and even small misplacement in the eye can result in sub-optimal vision correction. As a result, many patients are subject to inconvenient post-operative strategies to cope.

SUMMARY

This application is directed to providing a better outcome for patients undergoing intraocular refractive vision correction. This application discloses devices that can simplify treatment of complex cases, such as patients who have a lack of accommodation, cataract, and/or astigmatism.

In one embodiment, an intraocular lens is provided that includes a refractive element and a mask. The refractive element has a first power in a first meridian and a second power greater than the first power in a second meridian. A magnitude of the first and second powers and a location of the first and second meridians are configured to correct astigmatism in a human eye. The mask is configured to block a substantial portion of light from passing through an annular region thereof and to permit a substantial portion of light to pass through a central aperture thereof to enhance an astigmatism correction rotational misplacement range.

In another embodiment, an intraocular lens is provided that includes a refractive element that is adapted to counter astigmatism in a human eye and a mask. The mask is configured to prevent light from passing through an annular region thereof. The mask is configured to permit a light to pass through a central aperture thereof to increase depth of focus and to increase tolerance to rotational misplacement within the eye by as much as 15 degrees.

In another embodiment a method of correcting astigmatism is provided. In the method, an intraocular lens is placed into an eye of a patient. The intraocular lens has a cylinder power component aligned with a meridian thereof and a mask comprising a small aperture surrounded by an opaque member. It is then confirmed that the meridian of the intraocular lens is aligned within a range exceeding five degrees of a locally minimum power of the eye to reduce astigmatism in the eye such that the eye achieves functional acuity.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIGS. 4A-4D illustrate an embodiment of an IOL having a refractive element and a mask coupled with the refractive element.

FIG. 8 shows simulated cylinder performance of a monofocal IOL with corneal aberration correction compared with the same IOL additionally incorporating a small aperture optic.

DETAILED DESCRIPTION

A patient with astigmatism has unequal optical power at different rotational positions of the eye. The power of the eye is greater in some meridians of the eye than in other meridians. Patients who undergo IOL implantation surgery may suffer from astigmatism. This may be because even if the IOL has perfectly symmetric optics, the cornea of the eye in which the IOL is placed may be formed in a way providing uneven, rotationally asymmetric powers.

Figure 1:
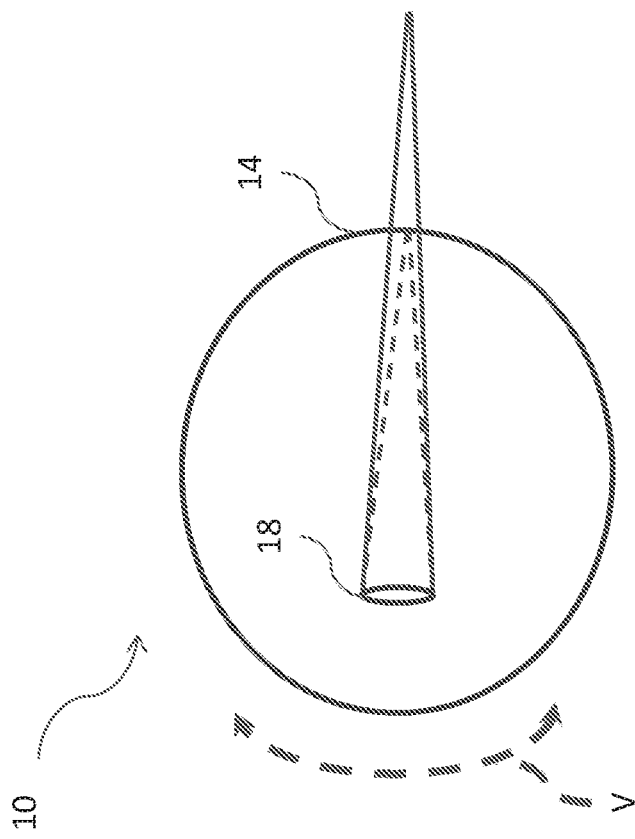
FIG. 1 schematically illustrates uncorrected and corrected focusing effect along a horizontal meridian of an eye with astigmatism in which the lowest power meridian of the eye is aligned with the horizontal meridian.
Figure 2:
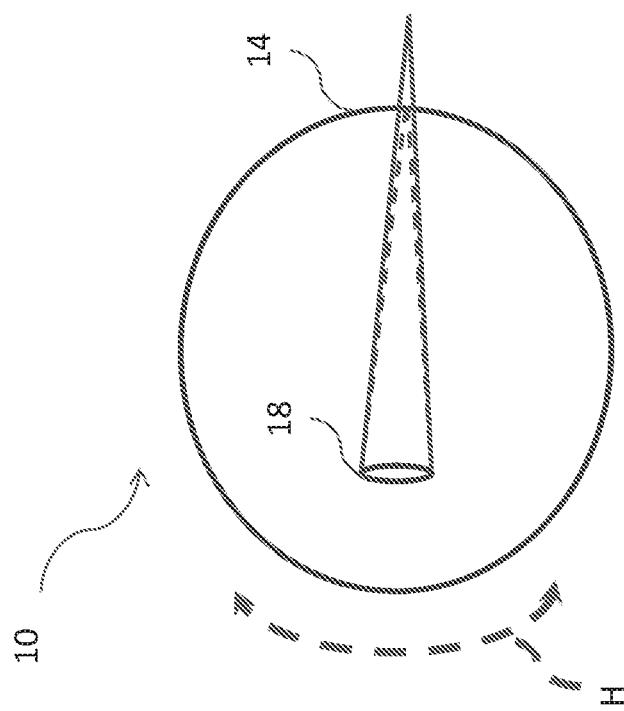
FIG. 2 schematically illustrates uncorrected and corrected focusing effect along a vertical meridian of an eye with astigmatism in which the highest power meridian of the eye is aligned with the vertical meridian.

FIGS. 1 and 2 illustrate a simple example of how an astigmatic eye 10 converges light passing through the lens. FIG. 1 illustrates a horizontal meridian H of the eye 10. Light incident on the horizontal meridian passes through the crystalline lens 18 and converges behind the retina 14. The solid lines show that the light passing along the horizontal meridian H is focused at a location rearward of the retina 14 by a first amount. FIG. 2 illustrates a vertical meridian V of the eye 10. In FIG. 2, solid lines illustrate that light passing along the vertical meridian V is focused at a location rearward of the retina 14 by a second amount greater than the first amount, which is the optical effect of astigmatism.

Figure 3:
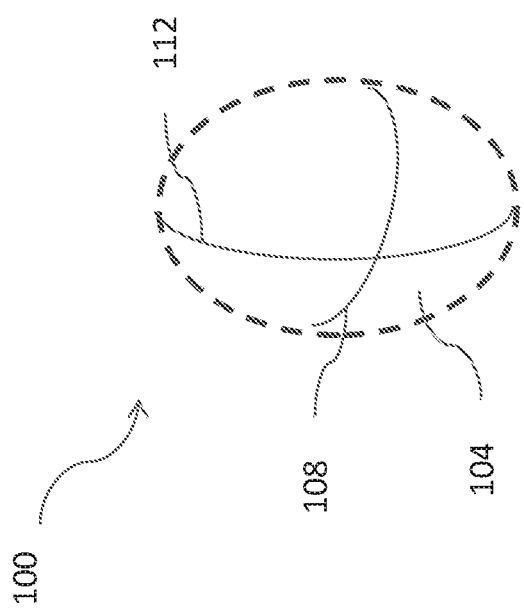
FIG. 3 illustrates a power distribution of a refractive element of an intraocular lens (IOL) configured to correct for rotationally asymmetric refractive error illustrated in FIGS. 1 and 2.

FIG. 3 shows a refractive element 100 that can correct for the rotational asymmetry of refractive power in an eye that causes astigmatism. The refractive element 100 includes a surface 104 that has a refractive power. That is, the surface 104 is configured to cause rays being refracted in an astigmatic eye and through the element 100 to converge at a common focal point. The surface 104 can have a refractive index that causes such convergence, can be curved to cause such convergence or can combine refractive index and curvature together or with other optical effects to cause such convergence. In one embodiment, the surface 104 has a first curvature 108 and a second curvature 112. The first curvature 108 is less than the second curvature 112. As a result, the first curvature 108 has less optical power than the second curvature 112. The second curvature 112 induces more convergence of the rays that are incident on the surface 104 along a line of the second curvature 112 than the first curvature 108.

If the refractive element 100 is properly placed in the astigmatic eye 10 illustrated in FIGS. 1 and 2, the refractive element 100 can correct the astigmatism. The refractive element 100 can be placed in the eye 10 such that the first curvature 108 is aligned with the horizontal meridian H which is illustrated in FIG. 1. When so placed, the first curvature 108 corrects the relatively smaller hyperopic error on the horizontal meridian H of the eye 10 by a first amount. The refractive element 100 can be placed in the eye 10 such that the second curvature 112 is aligned with the vertical meridian V which is illustrated in FIG. 2. When placed such that the second curvature 112 is aligned with the vertical meridian, the relatively larger hyperopic error is corrected by a larger amount than was corrected in the horizontal meridian H. As a result, the rays on both meridians are brought into focus at the same location. An additional power can be provided if needed to shift the focal plane to the retina as illustrated by the solid converging lines in FIGS. 1 and 2.

FIG. 3 shows the refractive element 100 surrounded by dashed lines. As discussed further below, other components of an IOL incorporating the refractive element 100 can be coupled with the refractive element 100 either prior to implantation or during the course of the useful life of the IOL incorporating the refractive element 100.

Intraocular Lens

As shown in FIGS. 4A-4D, an intraocular lens 1000 includes an optic 1004 and a mask 1012. The optic 1004 can be formed from an optically transmissive material, while the mask 1012 can be formed from an opaque material. The optic 1004 can include the refractive element 100 to correct refractive errors, such as rotationally asymmetric power, e.g., astigmatism. The optic 1004 can include other structures to improve the overall visual performance of the IOL 1000 in addition to the refractive element 100.

The optic 1004 can be monofocal or multifocal and it can have positive or negative optical power. The optic 1004 may be aspheric or any other configuration as the context may dictate. In various embodiments the optic 1004 has a cylinder power or other rotationally asymmetric power such that the optic 1004 can correct for astigmatism of an eye as discussed above. In some implementations, the greatest thickness of the optic 1004 is at the center of the optic 1004. In other implementations, the optic 1004 may have a reduced thickness at its center, which is further described in U.S. Publication No. 2011/0040376, filed Aug. 13, 2010, which is hereby incorporated by reference in its entirety herein. The optic 1004 may be substantially circular with an outer diameter between about 5.0 mm and about 8.0 mm, such as about 6.0 mm. A central thickness of the optic 1004 can be less than or equal to about 1.0 mm, such as between about 0.75 mm and about 1.0 mm.

The intraocular lens 1000 may include one or more haptics 1008 (e.g., one, two, three, four, or more) to prevent the intraocular lens 1000 from moving or rotating within the eye. As used herein the term "haptic" is intended to be a broad term encompassing struts and other mechanical structures that can be apposed against an inner surface of an eye and mounted to an optic to securely position an intraocular lens in an optical path of an eye. The haptics 1008 can be a variety of shapes and sizes depending on the location the intraocular lens 1000 is implanted in the eye. The haptics 1008 may be C-shaped, J-shaped, plate design, or any other design. The haptics 1008 may be manufactured substantially flat or vaulted with respect to the optic. Variations on the shape of the optic and the haptics can be found in U.S. Publication No. 2011/0040376, filed Aug. 13, 2010, which is hereby incorporated by reference in its entirety herein.

The mask 1012 can be formed on an anterior surface 1016 of the optic 1004 (see FIGS. 4A-4D), on a posterior surface 1020 of the optic 1004, or embedded within the optic 1004. When the mask 1012 is embedded within the optic 1004, the mask 1012 can be formed substantially at the midway line between the posterior 1020 and anterior surfaces 1016 of the optic 1004. But the mask 1012 can also be formed at other locations within the optic 1004. Additional information regarding the manufacturing of such intraocular lenses can be found in PCT/US2016/055207, filed Oct. 3, 2016, which is hereby incorporated by reference in its entirety herein.

Mask

Figure 5B:
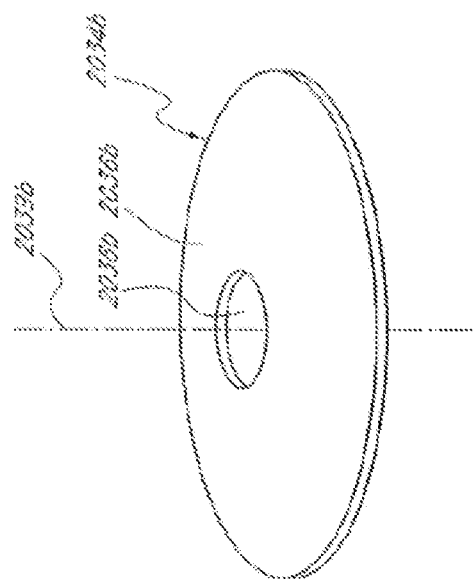
FIG. 5B illustrates another embodiment of the mask.
Figure 5A:
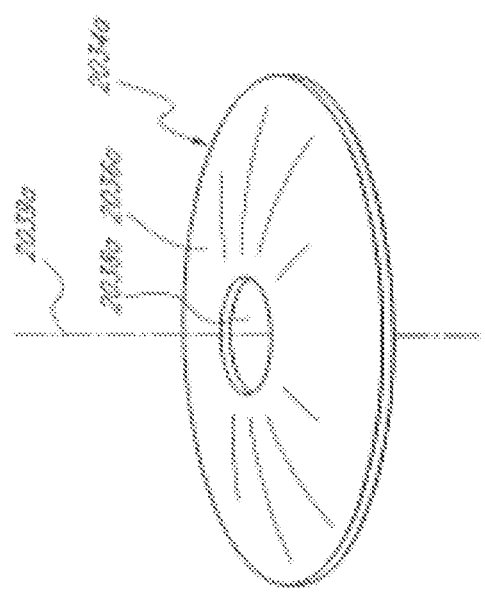
FIG. 5A illustrates an embodiment of a mask.

FIG. 5A illustrates a mask 2034a having an annular region 2036a surrounding an aperture 2038a substantially centrally located on the mask 2034a. An anterior surface of the annular region 2036a can have a curvature from the outer periphery to the inner periphery of the annular region 2036a, and the posterior surface of the annular region 2036a can have a similar curvature. FIG. 5B shows that the mask 2034b can be flat in some embodiments. The mask 2034b can include an annular region 2034b surrounding an aperture 2038b substantially centered on the optical axis 2039b of the mask 2034b. Although the features described below are described with respect to the mask 2034a, one or the more of the features may be applied to the mask 2034b.

In some embodiments, the outer periphery of the mask 2034a is generally circular with an outer diameter of at least about 3 mm and less than about 6 mm. In some embodiments, the diameter of the outer periphery of the mask 2034a is at least about 3 mm and less than or equal to about 4 mm.

A thickness of the mask 2034a can be constant or can vary between the inner periphery (near the aperture) and the outer periphery. For example, the thickness may increase from an outer periphery and/or inner periphery of the mask 2034a and toward a radial midline of the annular region 2036a. In general, the thickness at any location of the mask 2034a can be less than or equal to about 200 microns, or less than or equal to about 100 microns, but preferably between about 1 micron and about 20 microns. For example, the thickness of the mask 2034a can be within the range: from about 1 micron to about 40 microns, from about 5 microns to about 20 microns, from about 5 microns to about 15 microns. In some implementations, the thickness of the mask 2034a can be within about two microns of: about 15 microns, about 10 microns, about 8 microns, or about 5 microns.

The aperture 2038a can transmit substantially all incident visible light along the optical axis 2039a. For example, the aperture 2038a can be a through-hole in the annular region 2036a or a substantially light transmissive (e.g., transparent to visible light) portion thereof. The aperture 2038a can be substantially circular and/or substantially centered around the optical axis 2039a of the mask 2034a. The size of the aperture 2038a can be any size that is effective to increase the depth of focus of an eye of a patient with presbyopia. In particular, the size of the aperture 2038a can be dependent on the location of the mask 2034a within the eye (e.g., distance from the retina). In some implementations, the aperture 2038a can have a diameter of at least about 0.85 mm and less than or equal to about 2.8 mm, at least about 1.1 mm and less than or equal to about 1.6 mm, or at least about 1.3 mm and less than or equal to about 1.4 mm.

Figure 6:
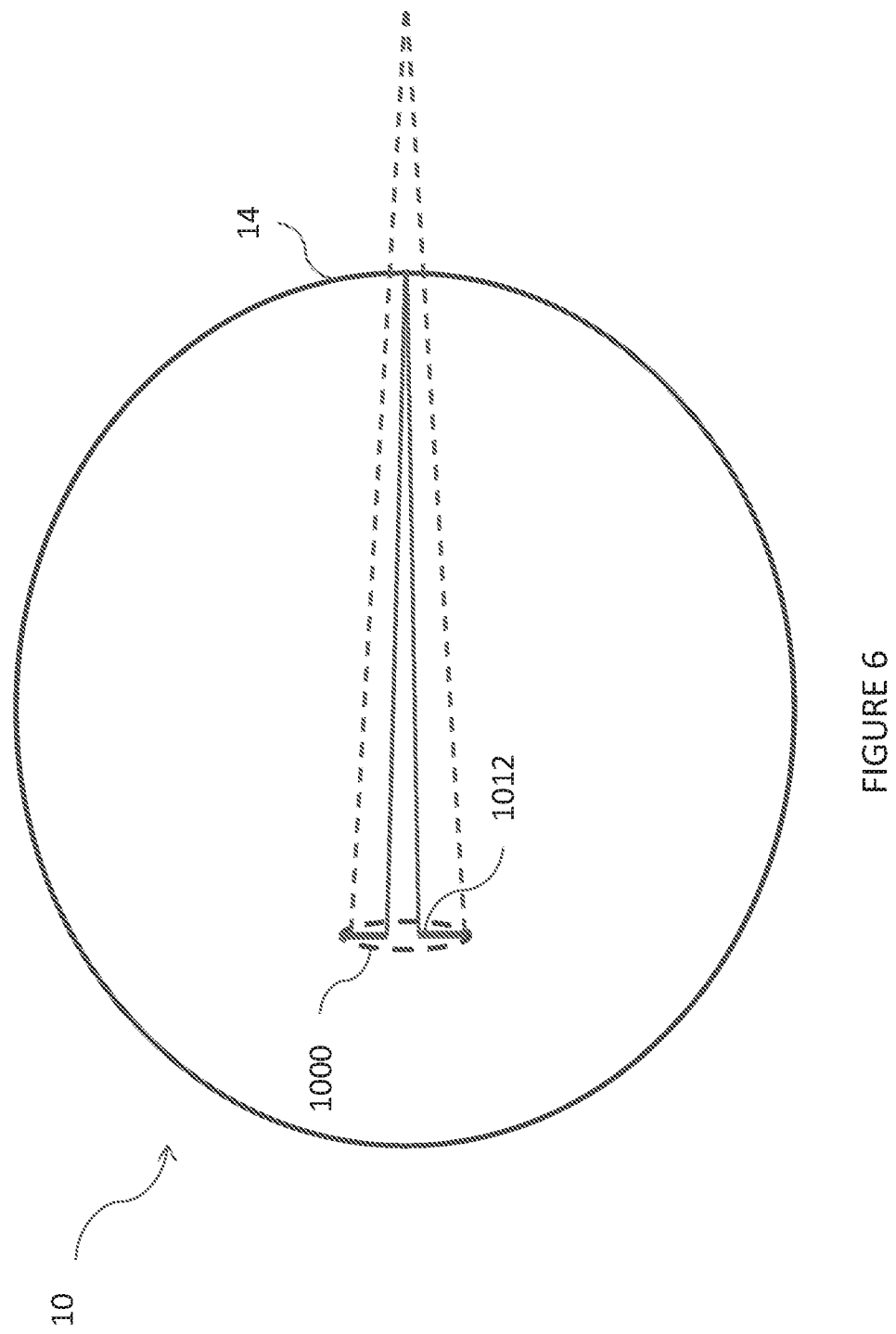
FIG. 6 schematically illustrates the depth of focus extending effect of the masks of FIGS. 5A and 5B.

The annular region 2036a can prevent transmission of substantially all or at least a portion of the spectrum of the incident visible light (e.g., radiant energy in the electromagnetic spectrum that is visible to the human eye) and/or the spectrum of non-visible light (e.g., radiant energy outside the range visible to humans). Preventing transmission of visible light through the annular region 2036a can block light that would not converge at the retina and fovea to form a sharp image. FIG. 6 illustrates this effect. In particular, the IOL 1000 is placed in the capsular bag of the eye 10. The mask 1012 is centered on the optical axis of the eye 10. Rays that would not converge on the retina 14 are illustrated by the dash lines. These rays are blocked by the annular region 2036a or the annular region 2036b of the mask 1012 and thus are prevented from degrading vision by causing a blur on the retina. Rays that converge on the retina 14 pass through the aperture of the mask 1012. A crisp image over a range of distances is provided by this focused light as discussed further below.

In some implementations, the annular region 2036a can prevent transmission of at least about: 90 percent of incident visible light, 92 percent of incident visible light, 95 percent of incident visible light, 98 percent of all incident visible light, or 99 percent of all incident visible light. The annular region 2036a can transmit no more than about: 10 percent of incident visible light, 8 percent of incident visible light, percent of incident visible light, 3 percent of incident visible light, 2 percent of incident visible light, or 1 percent of incident visible light.

In some embodiments, opacity of the annular region 2036a is achieved because the material used to make mask 2034a is naturally opaque. In other embodiments, the material used to make the mask 2034a may be naturally substantially clear but treated with a dye or other pigmentation agent (e.g., carbon black). In some embodiments, the mask is made of the same material as the lens body, with the addition of dye or other pigmentation agent. In other embodiments, the mask is made of a different material from the lens body.

Further variations of masks can be found in U.S. application Ser. No. 62/237,429, filed Oct. 5, 2015, U.S. Pat. No. 7,628,810, filed May 26, 2004, U.S. Publication No. 2012/0143325, filed Feb. 19, 2012, U.S. Publication No. 2011/0040376, filed Aug. 13, 2010; U.S. Publication No. 2013/0268071, filed Nov. 30, 2012; U.S. Publication No. 2014/0264981; U.S. Publication No. 2015/0073549, filed Aug. 7, 2014; U.S. Pat. No. 5,662,706, filed Jun. 14, 1996; U.S. Pat. No. 5,905,561, filed Jun. 14, 1996; and U.S. Pat. No. 5,965,330, filed Dec. 6, 1996, all of which are hereby incorporated by reference in their entirety herein.

Discussion of Simulation Tests

Figure 7:
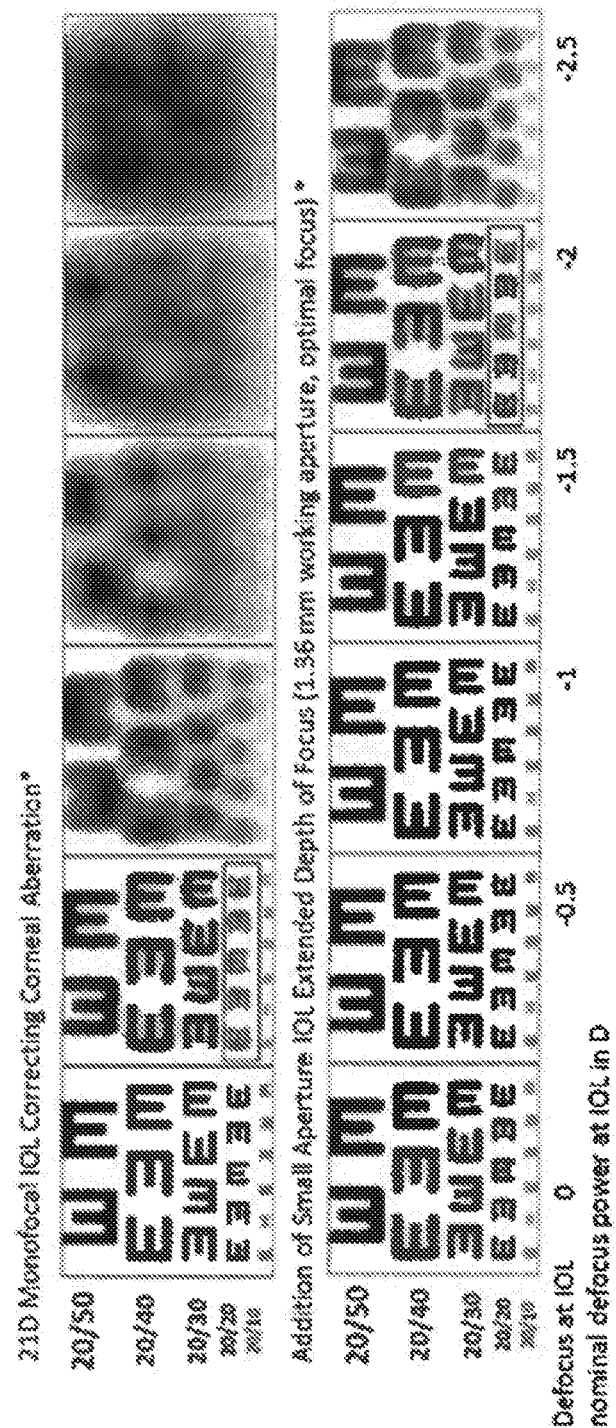
FIG. 7 shows simulated defocus performance of a monofocal IOL with corneal aberration correction compared with the same IOL additionally incorporating a small aperture optic.

FIG. 7, upper row, is a Zemax optical simulation of the optical performance of a 21 diopter monofocal IOL. In the simulation, corneal aberration is corrected and the simulation assumes a realistic polychromatic model eye, with a 3 mm pupil. The left-most box shows the visual acuity for 0 diopter defocus. The acuity illustrated is acceptable at 20/20 or greater. The second box from the left shows the visual acuity for a −0.5 diopter defocus using the same lens and model used in the left-most box. One can see that the performance has declined, but the threshold acuity level is still at about 20/20. The third box from the left shows the visual acuity for a −1.0 diopter defocus using the same lens and simulation model used in generating the left-most box. One can see that this box does not register any level of visual acuity and thus the IOL is completely ineffective at this and greater defocus amounts.

FIG. 7, lower row, is a Zemax optical simulation of the optical performance of an IOL that has a small aperture mask disposed therein for extended depth of focus. The small aperture optic can have a 1.36 mm working aperture. The IOL had optimal focus. The simulation used a realistic polychromatic model eye with a 3 mm pupil. The left-most box shows the visual acuity for 0 diopter defocus, which is acceptable at 20/20 or greater. In contrast to the upper row, each of the defocus positions in the lower row from the left most box toward the right from −0.5 diopter, −1.0 diopter, −1.5 diopter and −2.0 diopter defocus show a 20/20 visual acuity or better. This simulation confirms the effectiveness of the small aperture optic illustrated in FIG. 6.

FIG. 8, upper row, is a Zemax optical simulation of the optical performance of a 21 diopter monofocal IOL correcting corneal aberration using a realistic polychromatic model eye, with a 3 mm pupil. The left-most box shows the visual acuity for 0 diopter added cylinder power. The acuity illustrated is acceptable at 20/20 or greater. The third box from the left shows the visual acuity for a −0.5 diopter addition of cylinder power using the same lens and model used in the left-most box. One can see that the performance has declined, but the threshold acuity level is still at about 20/20. The fifth box from the left shows the visual acuity for a −1.0 diopter addition of cylinder power using the same lens and model used in the left-most box. One can see that this box does not register any useful level of visual acuity and thus the IOL is completely ineffective at this and greater amounts of cylinder.

FIG. 8, lower row, is a Zemax optical simulation of an IOL with a small aperture mask that provides extended depth of focus. The mask was provided with a 1.36 working aperture and the IOL with optimal focus. The model again was constructed using a realistic polychromatic model eye with a 3 nm pupil. The left-most box shows the visual acuity for 0 added cylinder power and in this box the acuity illustrated is acceptable at 20/20 or greater. The third and fifth boxes from the left show the visual acuity for a −0.5 and −1.0 diopter added cylinder power using the same lens and model used in the left-most box, lower row. One can see that the performance has declined, but the threshold acuity level is still at about 20/20. In fact the performance of the small aperture IOL remains acceptable even to the right-most box which illustrates performance with −1.5 diopter of cylinder. FIG. 8 thus shows that a small aperture IOL can provide vision correction for small amounts of astigmatism even up to −1.5 diopters of added cylinder.

Figure 9:
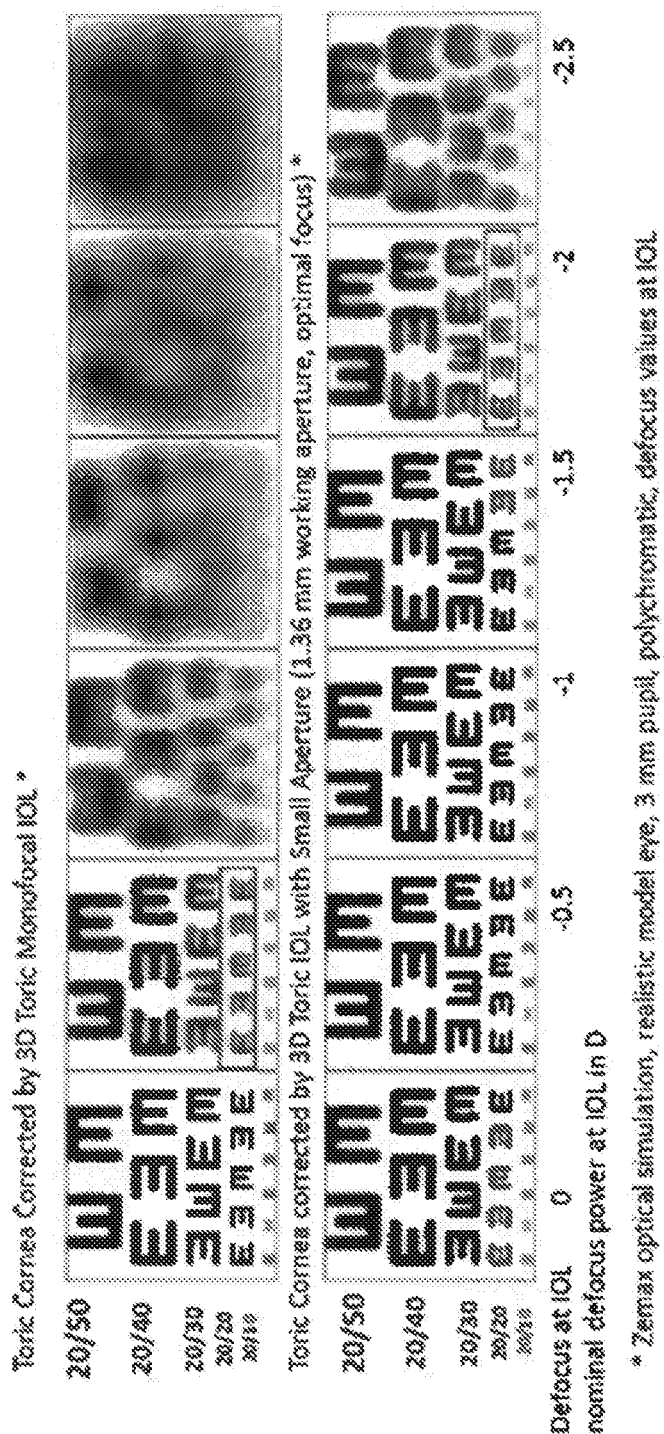
FIG. 9 shows simulated defocus performance of a monofocal toric IOL in an eye system with cylinder cornea compared with the same IOL additionally incorporating a small aperture optic.

FIG. 9 shows the performance of a toric IOL. In particular, FIG. 9, upper row, is a Zemax optical simulation of the optical performance of a 3 diopter toric monofocal IOL using a realistic polychromatic model eye, with a 3 mm pupil and with a toric cornea. The performance of the toric IOL is similar to that of the monofocal IOL illustrated in FIG. 7. That is, it can tolerate about −0.5 diopter defocus. But greater amounts of defocus degrade the visual acuity too much for the toric IOL to provide functional visual acuity. In contrast, FIG. 9, lower row, shows that astigmatism in an eye can be more robustly corrected by a 3 diopter toric IOL with a small aperture optic, e.g., having a 1.36 mm working aperture with the IOL having optimal focus. The lower row shows that the toric IOL with small aperture optic can still perform well at up to −2.0 diopters of defocus.

Figure 10:
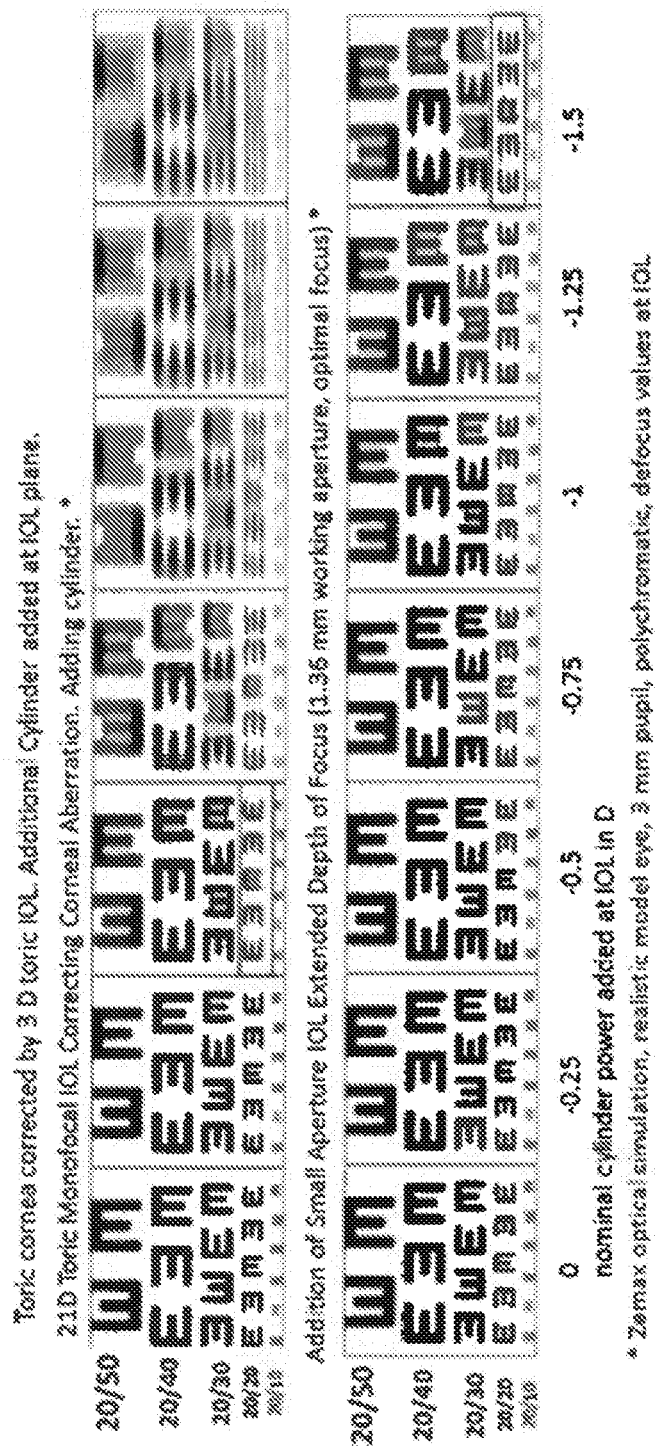
FIG. 10 shows simulated cylinder performance of a monofocal toric IOL in an eye system with cylinder at the cornea and additional cylinder at the IOL plane compared with the same IOL additionally incorporating a small aperture optic.

FIG. 10 shows a further comparison of the performance of a 21 diopter monofocal toric IOL and the same IOL with a small aperture optic, e.g., an optic having a 1.36 mm working aperture. FIG. 10 shows the ability of these two IOLs to sustain visual acuity when working with progressively more additional cylinder power. The upper row shows that a toric IOL can sustain acceptable visual acuity up to an additional −0.5 diopter of cylinder. The lower row shows that the toric IOL with a small aperture optic can perform well even when subject to up to −1.5 diopter of cylinder. This means that even in a patient with progressively worsening astigmatism, the toric IOL with small aperture optic can continue to provide good vision without additional lenses or procedures for much longer than the standard toric IOL.

Figure 11:
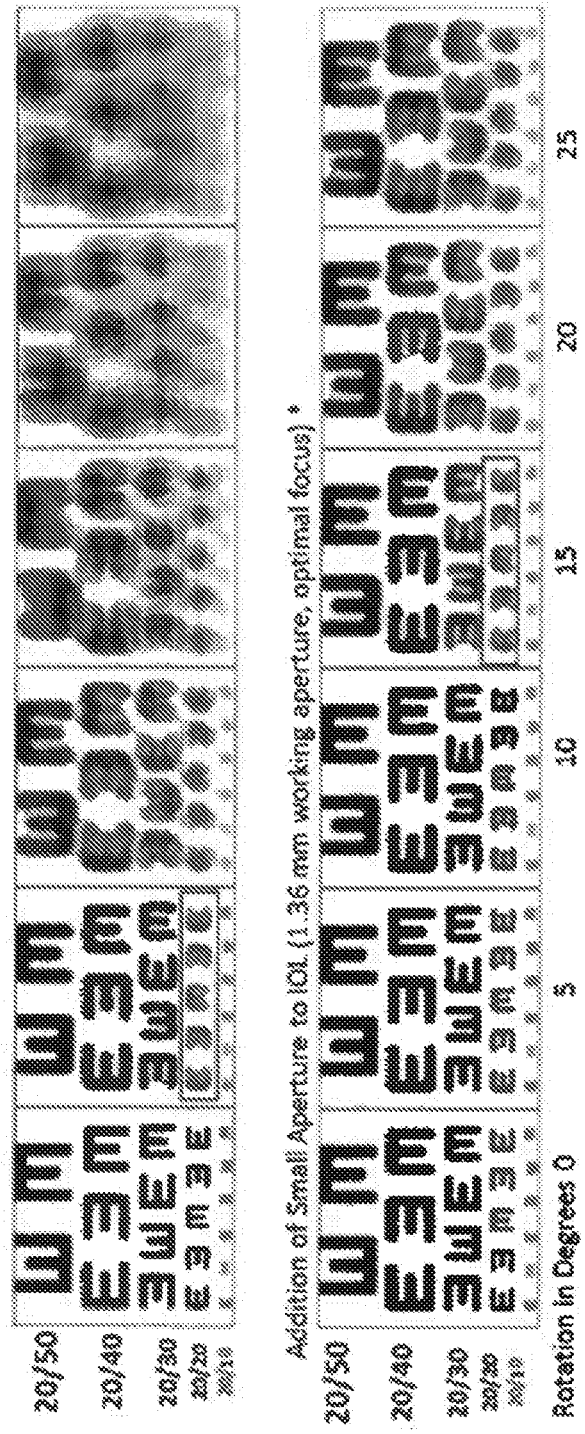
FIG. 11 shows simulated rotational misalignment performance of a monofocal toric IOL in an eye system with cylinder at the cornea compared with the same IOL additionally incorporating a small aperture optic.

FIG. 11 shows a further comparison of the performance of a 21 diopter monofocal toric IOL and the same IOL with a small aperture optic, an optic having a 1.36 mm working aperture. FIG. 11 shows the ability of these two IOLs to sustain rotational misplacement. The upper row shows that a toric IOL can sustain a 5 degree rotational misplacement or misalimment. Beyond this amount, the visual acuity delivered by the standard toric IOL is insufficient. The lower now shows that the toric IOL with a small aperture optic can perform well at up to 15 degrees of rotational misplacement or misalignment. This means that even where an IOL implantation procedure was not according to a pre-operative plan, the IOL will perform well. This is because the IOL has a much wider window of acceptable rotational placement. The lower row of FIG. 11 suggests that a 30 degree window can be provided within which a patient will have acceptable visual acuity. This is three times larger than the much more limited range of placement that a standard IOL can tolerate. This represents a significant improvement in toric IOL design, enhancing the robustness of the IOL such that the chance of a poor outcome even if placement is sub-optimal is greatly reduced.

The simulation performance can be summarized as follows:

| | IOL Configuration | | | |
| --- | --- | --- | --- | --- |
| Performance Measurement | Standard Monofocal IOL | Standard Monofocal Toric IOL | EDOF Small Aperture IOL | EDOF Small Aperture Toric IOL |
| Tolerance to Astigmatism | ≤0.5 D | ≤0.5 D | ≤1.5 D | ±≤1.5 D |
| Tolerance to Angular Rotational Placement | N/A | ±≤5° | N/A | ±≤15° |
| Depth of Focus | ±≤0.5 D | ±≤0.5 D | ±≤2.0 D | ±≤2.0 D |

Figure 12:
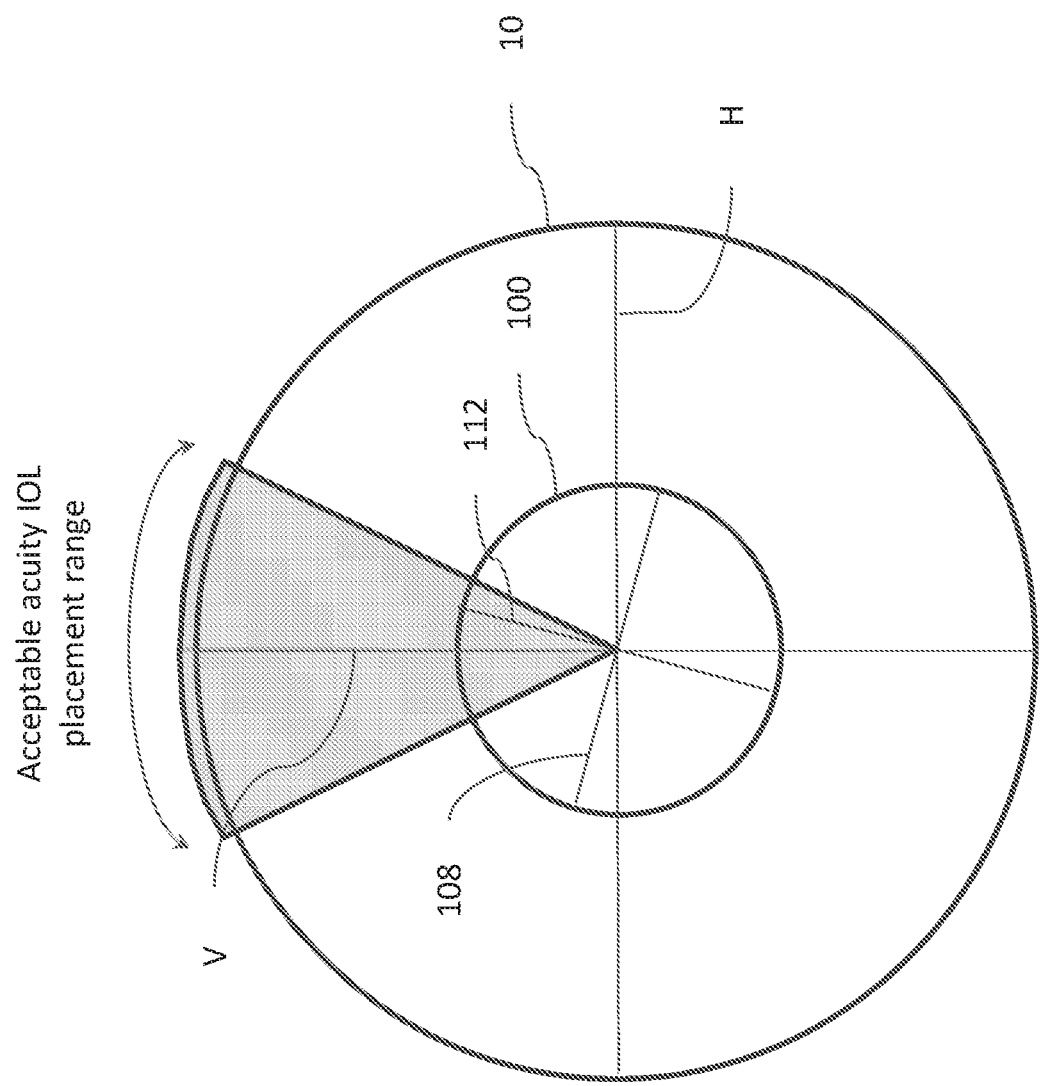
FIG. 12 is a schematic diagram of an eye showing increased tolerance to misplacement as provided by certain embodiments herein.

FIG. 12 schematically illustrates aspects of certain embodiments. In particular, a cylinder power exists in the eye 10 prior to correction causing astigmatism. In this case, the power in the vertical meridian V is noticeably less than in the horizontal meridian H. The IOL 1000 including the refractive element 100 is provided and is placed in the eye 10. As discussed above, the refractive element 100 has different powers in different portions. For example, a meridian of the refractive element 100 can have the first curvature 108 and another meridian of the element 100 can have the second curvature 112 larger than the first curvature. The curvatures 108, 112 are along perpendicular meridians, but could be at other angles to each other as a function of the power profile of the eye. As discussed above, the steeper second curvature 112 induces more convergence. Accordingly, the second curvature 112 should optimally be aligned with the vertical meridian V of the eye 10 so that the locally lower power of the eye 10 is compensated by the second curvature 112 to enable the vertical and horizontal meridians V, H to converge at the same location. However, as shown, the refractive element 100 is rotationally offset from the optimal aligned position. Advantageously, the IOL 1000 is enabled by the combination of a tone configuration of the refractive element 100 and the mask 1012 to have a much larger than conventional acceptable rotational offset from the optimal position. FIG. 12 shows in the shaded pie-shaped region that there is an acceptable acuity over a large IOL placement range. In this embodiment, the range extends on both sides, e.g., symmetrically, of the optimal (vertical) position. As such IOL 1000 provides an increase in tolerance to rotational misplacement. The range extends beyond the angle of misplacement of the IOL 1000. In the conventional IOL, the range would be much less, for example between the position of the second curvature 112 and the vertical meridian V preventing the convention IOL when placed as shown in FIG. 12 from providing functional visual acuity.

Terminology

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The terms "approximately," "about," and "substantially" as used herein represent an amount close to the stated amount that still performs a desired function or achieves a desired result. For example, the terms "approximately," "about," and "substantially" may refer to an amount that is within less than 10% of the stated amount, as the context may dictate.

The ranges disclosed herein also encompass any and all overlap, sub-ranges, and combinations thereof. Language such as "up to," "at least," "greater than," "less than," "between" and the like includes the number recited. Numbers preceded by a term such as "about" or "approximately" include the recited numbers. For example, "about 3 mm" includes "3 mm."

Although certain embodiments and examples have been described herein, it will be understood by those skilled in the art that many aspects of the methods and IOL shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

What is claimed is:

1. An intraocular lens comprising:
   a toric refractive element adapted to counter astigmatism in a human patient's eye;
   one or more haptics configured to position the intraocular lens in the eye, the one or more haptics extending from a fixed end disposed at a periphery of the toric refractive element to a free end adapted to contact an inner surface of the eye, the one or more haptics forming an anterior edge of the intraocular lens when implanted in the eye; and
   a mask configured to prevent a substantial portion of light from passing through an annular region thereof and to permit light to pass through a central aperture thereof to increase depth of focus, a diameter of the central aperture is at least 0.85 mm and less than or equal to 2.8 mm,
   wherein a combination of the toric refractive element and the mask is configured to increase tolerance to rotational misplacement within the patient's eye within a 30 degree window.

2. The intraocular lens of claim 1, wherein the mask is coupled with a face of an optic incorporating the mask.

3. The intraocular lens of claim 2, wherein the mask is formed on a piggyback IOL configured to couple with the eye to place the mask on the face of the optic.

4. The intraocular lens of claim 1, wherein the mask is embedded in an optic comprising the refractive element.

5. The intraocular lens of claim 1, wherein the mask comprises a plurality of small holes disposed through the annular region to secure the mask to an optic including the refractive element.

6. The intraocular lens of claim 1, wherein the mask is configured to increase depth of focus by a magnitude equivalent to up to 2 diopters of add power.

7. The intraocular lens of claim 1, wherein the refractive element comprises a rotational alignment feature.

8. The intraocular lens of claim 1, wherein the intraocular lens is configured to maintain visual acuity of at least 20/20 from 0.0 diopters to +/− 2.0 diopters of defocus.

9. The intraocular lens of claim 1, wherein the mask comprises an elastic material.

10. The intraocular lens of claim 1, wherein the 30 degree window is +/− 15 degrees.

11. The intraocular lens of claim 1, wherein the intraocular lens is a monofocal intraocular lens.

12. The intraocular lens of claim 1, wherein the one or more haptics are vaulted with respect to the refractive element.

13. The intraocular lens of claim 1, wherein the one or more haptics are flat with respect to the refractive element.

14. An intraocular lens comprising:
    a toric refractive element adapted to counter astigmatism in a human patient's eye;
    one or more haptics configured to position the intraocular lens in the eye, the one or more haptics extending from a fixed end disposed at a periphery of the toric refractive element to a free end adapted to contact an inner surface of the eye, the toric refractive element forming an anterior edge of the intraocular lens when implanted in the eye; and
    a mask configured to block a substantial portion of light from passing through an annular region thereof and to permit a substantial portion of light to pass through a central aperture thereof to increase depth of focus;

wherein the intraocular lens is configured to maintain visual acuity of at least 20/20 within +/− 15 degrees of rotational misplacement.

15. The intraocular lens of claim 14, wherein the one or more haptics are vaulted with respect to the refractive element.

16. The intraocular lens of claim 14, wherein the one or more haptics are flat with respect to the refractive element.

* * * * *

UNITED STATES PATENT AND TRADEMARK OFFICE
CERTIFICATE OF CORRECTION

PATENT NO. : 11,464,625 B2
APPLICATION NO. : 15/775158
DATED : October 11, 2022
INVENTOR(S) : William J. Link et al.

It is certified that error appears in the above-identified patent and that said Letters Patent is hereby corrected as shown below:

In the Specification

In Column 2, Line 63, delete "tonic" and insert --toric--.

In Column 2, Line 67, delete "tonic" and insert --toric--.

In Column 6, Line 4, after "light," insert --5--.

In Column 7, Line 26, delete "tonic" and insert --toric--.

In Column 7, Line 28, delete "tonic" and insert --toric--.

In Column 7, Line 30, delete "tonic" and insert --toric--.

In Column 7, Line 34, delete "tonic" and insert --toric--.

In Column 7, Line 36, delete "tonic" and insert --toric--.

In Column 7, Line 39, delete "tonic" and insert --toric--.

In Column 7, Line 47, delete "tonic" and insert --toric--.

In Column 7, Line 58, after "optic," insert --e.g.,--.

In Column 7, Line 61, delete "tonic" and insert --toric--.

In Column 7, Line 62, delete "misalimment." and insert --misalignment.--.

In Column 7, Line 63, delete "tonic" and insert --toric--.

Signed and Sealed this
Tenth Day of January, 2023

*Katherine Kelly Vidal*
Katherine Kelly Vidal
*Director of the United States Patent and Trademark Office*

In Column 7, Line 64, delete "now" and insert --row--.

In Column 9, Line 34, delete "IOL shown" and insert --IOLs shown--.